(12) United States Patent
Bartsch et al.

(10) Patent No.: US 6,555,733 B2
(45) Date of Patent: Apr. 29, 2003

(54) GENES CODING FOR AMINO ACID DEACETYLASES WITH SPECIFICITY FOR N-ACETYL-L-PHOSPHINOTHRICIN, THEIR ISOLATION AND USE

(75) Inventors: Klaus Bartsch, Königstein (DE); Guido Kriete, Halle (DE); Inge Broer, Roggentin (DE); Alfred Pühler, Bielefeld (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/727,238

(22) Filed: Nov. 30, 2000

(65) Prior Publication Data

US 2001/0052139 A1 Dec. 13, 2001

Related U.S. Application Data

(62) Division of application No. 09/319,892, filed as application No. PCT/EP97/06755 on Dec. 3, 1997, now Pat. No. 6,177,616.

(30) Foreign Application Priority Data

Dec. 16, 1996 (DE) .......................... 196 52 284

(51) Int. Cl.$^7$ .................. C12N 15/05; C12N 15/31; C12N 15/63; C12N 15/82; A01H 5/00
(52) U.S. Cl. .................. 800/288; 800/278; 800/298; 800/295; 800/287; 800/303; 435/468; 435/419; 435/69.1; 435/252.2; 536/23.2; 536/23.7; 536/24.1
(58) Field of Search ............... 800/278, 288, 800/303, 298, 295, 287; 435/69.1, 252.2, 468, 419; 536/23.7, 24.1, 23.2

(56) References Cited

FOREIGN PATENT DOCUMENTS

| DE | 2 258 448 | 8/1975 |
|---|---|---|
| DE | 41 26 414 A | 2/1993 |
| DE | 0531716 | 3/1993 |
| DE | 43 08 061 | 9/1994 |
| DE | 196 39 463 | 4/1998 |

OTHER PUBLICATIONS

Turgut et al, "The highly expressed tapetum–specifc A9 gene is not required for male fertility in *Brassica napus*", 1994, Plant Molecular Biology, vol. 24, No. 1, pp 97–102.*

Thorsness et al, "A brassica S–Locus Gene Promoter Targets Toxic Gene Expressions Cell Death to the Pistil and Pollen of Transgenic Nicotiana", 1991, Developmental Biology, vol. 143, pp. 173–184.*

Goldman et al, "Female . . . stigma–specific cell ablation", 1994, pp. 2976–2984.*

Kandasamy et al, "Ablation of Papilar . . . Stigma Receptivity to Pollination", 1993, The Plant Cell, vol. 5, pp. 262–275.*

Kriete et al., "Male Sterility in Transgeneic Tobacco Induced by Tapetum–Specific Decaetylation of the Externally Applied Non–toxic Compound n–acetyl–1–phophinothricin", Plant Journal, vol. 9, No. 6, 1996, pp. 809–828.

* cited by examiner

Primary Examiner—Elizabeth F. McElwain
Assistant Examiner—Medina A. Ibrahim
(74) Attorney, Agent, or Firm—Frommer Lawrence & Haug LLP

(57) ABSTRACT

The invention relates to DNA molecules which code for deacetylases or proteins having the biological activity of a deacetylase and also transgenic plant cells which were transformed using the DNA molecules according to the invention. These molecules can be used for the production of plants having specifically destroyable parts, i.e. male- or female-sterile plants, by means of the specific expression of a deacetylase gene.

17 Claims, 5 Drawing Sheets

SEQUENCE LISTING

<160> NUMBER OF SEQ ID NOS: 4

<210> SEQ ID NO 1
<211> LENGTH: 1320
<212> TYPE: DNA
<213> ORGANISM: Stenotrophomonas sp
<220> FEATURE:
<221> NAME/KEY: CDS
<222> LOCATION: (1)..(1317)
<223> OTHER INFORMATION: N-acetyl-PPT deacetylase coding sequence

<400> SEQUENCE: 1

```
atg atc cgc aag acc gtt ctg ttg act gcg ctg tcc tgc gcc ctg gcc        48
Met Ile Arg Lys Thr Val Leu Leu Thr Ala Leu Ser Cys Ala Leu Ala
1               5                   10                  15
```

-continued

| | |
|---|---|
| tcc gcg aca gcc acc gcc gcc gaa ggc cag cgg ccc gag gtg gag gcc<br>Ser Ala Thr Ala Thr Ala Ala Glu Gly Gln Arg Pro Glu Val Glu Ala<br>              20                     25                    30 | 96 |
| gcc gcc gcg cgc ctg cag cgg cag gtg gtg gag tgg cgc cgc gat ttc<br>Ala Ala Ala Arg Leu Gln Arg Gln Val Val Glu Trp Arg Arg Asp Phe<br>         35                     40                     45 | 144 |
| cac cag cat ccg gag ctg tcc aac cgc gag gtg cgc acc gcc gcc aag<br>His Gln His Pro Glu Leu Ser Asn Arg Glu Val Arg Thr Ala Ala Lys<br>      50                   55                     60 | 192 |
| gtg gcc gag cgc ctg cgc gcg atg ggc ctg caa ccg cag acc ggc gtc<br>Val Ala Glu Arg Leu Arg Ala Met Gly Leu Gln Pro Gln Thr Gly Val<br>65                     70                     75                     80 | 240 |
| gcc gtg cac ggc gtg gtg gcg atc atc aag ggc gcc ctg ccg ggg ccg<br>Ala Val His Gly Val Val Ala Ile Ile Lys Gly Ala Leu Pro Gly Pro<br>                    85                     90                     95 | 288 |
| aag atc gcc ctg cgc gcg gac atg gac gcg ctg ccg gtg acc gaa cag<br>Lys Ile Ala Leu Arg Ala Asp Met Asp Ala Leu Pro Val Thr Glu Gln<br>              100                    105                   110 | 336 |
| acc ggg ctg ccg ttc gcc tcc acc gcc acg gcc gag tac cgc ggc gag<br>Thr Gly Leu Pro Phe Ala Ser Thr Ala Thr Ala Glu Tyr Arg Gly Glu<br>         115                    120                   125 | 384 |
| aag gtc ggg gtg atg cat gcc tgc ggc cac gac gcc cat acc gcc acc<br>Lys Val Gly Val Met His Ala Cys Gly His Asp Ala His Thr Ala Thr<br>130                     135                   140 | 432 |
| ctc ctc ggc gtg gcc gac gcg ctg gtg gcc atg cgc gac acg ctg ccc<br>Leu Leu Gly Val Ala Asp Ala Leu Val Ala Met Arg Asp Thr Leu Pro<br>145                     150                   155                  160 | 480 |
| ggc gaa gta atg ctg atc ttc cag ccg gcc gag gaa ggc gcg ccg ccg<br>Gly Glu Val Met Leu Ile Phe Gln Pro Ala Glu Glu Gly Ala Pro Pro<br>                  165                    170                   175 | 528 |
| ccg gag cag ggc ggt gcc gag ctg atg ctc aag gag ggg ctg ttc aag<br>Pro Glu Gln Gly Gly Ala Glu Leu Met Leu Lys Glu Gly Leu Phe Lys<br>         180                    185                   190 | 576 |
| gag ttc aag ccg gag gcg gtg ttc ggc ctg cac gtg ttc tcc agc gtc<br>Glu Phe Lys Pro Glu Ala Val Phe Gly Leu His Val Phe Ser Ser Val<br>195                     200                   205 | 624 |
| cag gcc ggg cag atc gcc gtg cgc ggc ggc ccg ctg atg gcc gcc tcc<br>Gln Ala Gly Gln Ile Ala Val Arg Gly Gly Pro Leu Met Ala Ala Ser<br>         210                    215                   220 | 672 |
| gac cgc ttc gcc atc acc gtc aac ggc cgc cag acc cat ggc tcg gcg<br>Asp Arg Phe Ala Ile Thr Val Asn Gly Arg Gln Thr His Gly Ser Ala<br>225                     230                   235                  240 | 720 |
| ccc tgg aac ggc atc gat ccg att gtc gcc gcc tcc gac ctg atc ggc<br>Pro Trp Asn Gly Ile Asp Pro Ile Val Ala Ala Ser Asp Leu Ile Gly<br>                  245                    250                   255 | 768 |
| acc gcg cag acc atc gtc agc cgc cgc gcc aac ctg tcc aag cag ccg<br>Thr Ala Gln Thr Ile Val Ser Arg Arg Ala Asn Leu Ser Lys Gln Pro<br>         260                    265                   270 | 816 |
| gcg gtg ctg acc ttc ggc gcg atc aag ggc ggc atc cgc tac aac atc<br>Ala Val Leu Thr Phe Gly Ala Ile Lys Gly Gly Ile Arg Tyr Asn Ile<br>              275                    280                   285 | 864 |
| atc ccc gac tcg gtg gag atg gtc ggc acc atc cgc acc ttc gac ccg<br>Ile Pro Asp Ser Val Glu Met Val Gly Thr Ile Arg Thr Phe Asp Pro<br>         290                    295                   300 | 912 |
| gac atg cgc aag cag atc ttc gcc gac ttg cgc aac gtc gcc gag cac<br>Asp Met Arg Lys Gln Ile Phe Ala Asp Leu Arg Asn Val Ala Glu His<br>305                     310                   315                  320 | 960 |
| acc gct gcc gcg cat ggc gcc acc gcc acc acc gac atc tac gag aag<br>Thr Ala Ala Ala His Gly Ala Thr Ala Thr Thr Asp Ile Tyr Glu Lys | 1008 |

```
gac ggc aac ccg gcc acg gtc aac gac ccg gcg ctg acc gcg cgc atg      1056
Asp Gly Asn Pro Ala Thr Val Asn Asp Pro Ala Leu Thr Ala Arg Met
            340                 345                 350 ctg ccc agc ctg cag gcc gtg gtc ggc aag gac aac gtc tac gag ccg      1104
Leu Pro Ser Leu Gln Ala Val Val Gly Lys Asp Asn Val Tyr Glu Pro
        355                 360                 365 ccg ctg cag atg ggc tcg gag gac ttc tcg ctg tat gcg cag cag gtg      1152
Pro Leu Gln Met Gly Ser Glu Asp Phe Ser Leu Tyr Ala Gln Gln Val
    370                 375                 380 ccg gcg atg ttc ttc ttc gtc ggc tcc acc ggc gcg ggc atc gac ccg      1200
Pro Ala Met Phe Phe Phe Val Gly Ser Thr Gly Ala Gly Ile Asp Pro
385                 390                 395                 400 gcc acc gcg ccc agc aac cac tcg ccg aag ttc ctc ctc gac gag aag      1248
Ala Thr Ala Pro Ser Asn His Ser Pro Lys Phe Leu Leu Asp Glu Lys
                405                 410                 415 gcg ctg gac gtg ggc ctg cgc gcg ctg ctg cag gtg tcg ctg gac tat      1296
Ala Leu Asp Val Gly Leu Arg Ala Leu Leu Gln Val Ser Leu Asp Tyr
            420                 425                 430 ctg cac ggt ggc aag gcg ggg tga                                      1320
Leu His Gly Gly Lys Ala Gly
        435
```

<210> SEQ ID NO 2

<211> LENGTH: 439
<212> TYPE: PRT
<213> ORGANISM: Stenotrophomonas sp

<400> SEQUENCE: 2

```
Met Ile Arg Lys Thr Val Leu Leu Thr Ala Leu Ser Cys Ala Leu Ala
1               5                   10                  15

Ser Ala Thr Ala Thr Ala Ala Glu Gly Gln Arg Pro Glu Val Glu Ala
            20                  25                  30

Ala Ala Ala Arg Leu Gln Arg Gln Val Val Glu Trp Arg Arg Asp Phe
        35                  40                  45

His Gln His Pro Glu Leu Ser Asn Arg Glu Val Arg Thr Ala Ala Lys
    50                  55                  60

Val Ala Glu Arg Leu Arg Ala Met Gly Leu Gln Pro Gln Thr Gly Val
65                  70                  75                  80

Ala Val His Gly Val Val Ala Ile Ile Lys Gly Ala Leu Pro Gly Pro
                85                  90                  95

Lys Ile Ala Leu Arg Ala Asp Met Asp Ala Leu Pro Val Thr Glu Gln
            100                 105                 110

Thr Gly Leu Pro Phe Ala Ser Thr Ala Thr Ala Glu Tyr Arg Gly Glu
        115                 120                 125

Lys Val Gly Val Met His Ala Cys Gly His Asp Ala His Thr Ala Thr
    130                 135                 140

Leu Leu Gly Val Ala Asp Ala Leu Val Ala Met Arg Asp Thr Leu Pro
145                 150                 155                 160

Gly Glu Val Met Leu Ile Phe Gln Pro Ala Glu Gly Ala Pro Pro
                165                 170                 175

Pro Glu Gln Gly Gly Ala Glu Leu Met Leu Lys Glu Gly Leu Phe Lys
            180                 185                 190

Glu Phe Lys Pro Glu Ala Val Phe Gly Leu His Val Phe Ser Ser Val
        195                 200                 205

Gln Ala Gly Gln Ile Ala Val Arg Gly Gly Pro Leu Met Ala Ala Ser
```

-continued

```
            210                 215                 220
Asp Arg Phe Ala Ile Thr Val Asn Gly Arg Gln Thr His Gly Ser Ala
225                 230                 235                 240

Pro Trp Asn Gly Ile Asp Pro Ile Val Ala Ala Ser Asp Leu Ile Gly
                245                 250                 255

Thr Ala Gln Thr Ile Val Ser Arg Arg Ala Asn Leu Ser Lys Gln Pro
                260                 265                 270

Ala Val Leu Thr Phe Gly Ala Ile Lys Gly Gly Ile Arg Tyr Asn Ile
                275                 280                 285

Ile Pro Asp Ser Val Glu Met Val Gly Thr Ile Arg Thr Phe Asp Pro
            290                 295                 300

Asp Met Arg Lys Gln Ile Phe Ala Asp Leu Arg Asn Val Ala Glu His
305                 310                 315                 320

Thr Ala Ala His Gly Ala Thr Ala Thr Asp Ile Tyr Glu Lys
                325                 330                 335

Asp Gly Asn Pro Ala Thr Val Asn Asp Pro Ala Leu Thr Ala Arg Met
                340                 345                 350

Leu Pro Ser Leu Gln Ala Val Val Gly Lys Asp Asn Val Tyr Glu Pro
                355                 360                 365

Pro Leu Gln Met Gly Ser Glu Asp Phe Ser Leu Tyr Ala Gln Gln Val
            370                 375                 380

Pro Ala Met Phe Phe Phe Val Gly Ser Thr Gly Ala Gly Ile Asp Pro
385                 390                 395                 400

Ala Thr Ala Pro Ser Asn His Ser Pro Lys Phe Leu Leu Asp Glu Lys
                405                 410                 415

Ala Leu Asp Val Gly Leu Arg Ala Leu Leu Gln Val Ser Leu Asp Tyr
                420                 425                 430

Leu His Gly Gly Lys Ala Gly
            435
```

<210> SEQ ID NO 3
<211> LENGTH: 1273
<212> TYPE: DNA
<213> ORGANISM: Comamonas acidovorans
<220> FEATURE:
<221> NAME/KEY: CDS
<222> LOCATION: (1)..(1206)
<223> OTHER INFORMATION: coding sequence of the deacetylase gene from comamonas acidovoran

<400> SEQUENCE: 3

```
atg gcc ttg ctg cag gag ctg ctg gac agc gca ccc gag atc acc gcg    48
Met Ala Leu Leu Gln Glu Leu Leu Asp Ser Ala Pro Glu Ile Thr Ala
1               5                   10                  15 ctg cgc cgc gac ata cat gcc cat ccc gaa ctg tgc ttc gag gaa ctg    96
Leu Arg Arg Asp Ile His Ala His Pro Glu Leu Cys Phe Glu Glu Leu
            20                  25                  30 cgc acc gcc gac ctg gtg gcc cgg cag ctc gaa ggc tgg ggc att gcc   144
Arg Thr Ala Asp Leu Val Ala Arg Gln Leu Glu Gly Trp Gly Ile Ala
        35                  40                  45 gtg cac cgc ggc ctg ggc cgc acg ggc gtg gtg ggc acc atc cac ggc   192
Val His Arg Gly Leu Gly Arg Thr Gly Val Val Gly Thr Ile His Gly
    50                  55                  60 cgt gac ggc ggc gcc agc ggc cgg gcc atc ggg ctg cgc gcc gac atg   240
Arg Asp Gly Gly Ala Ser Gly Arg Ala Ile Gly Leu Arg Ala Asp Met
65                  70                  75                  80 gac gcc ctg ccc atg cag gag ttc aac acc ttc gag cac gcc agc cgc   288
Asp Ala Leu Pro Met Gln Glu Phe Asn Thr Phe Glu His Ala Ser Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 85  |     |     |     |     | 90  |     |     |     |     | 95  |     |      |
| cac | gcc | gga | aaa | atg | cat | gcc | tgc | gga | cat | gac | ggc | cat | gtc | gcc | atg | 336  |
| His | Ala | Gly | Lys | Met | His | Ala | Cys | Gly | His | Asp | Gly | His | Val | Ala | Met |      |
|     |     |     | 100 |     |     |     | 105 |     |     |     | 110 |     |     |     |     |      |
| ctg | ctg | gcc | gcc | gcg | cag | tac | ctg | gcc | gtg | cac | cgc | gac | agc | ttc | gag | 384  |
| Leu | Leu | Ala | Ala | Ala | Gln | Tyr | Leu | Ala | Val | His | Arg | Asp | Ser | Phe | Glu |      |
|     |     | 115 |     |     |     |     | 120 |     |     |     |     | 125 |     |     |     |      |
| ggc | acg | gtg | cac | ctg | atc | ttc | cag | ccg | gcc | gaa | gag | ggc | ggc | ggc | ggg | 432  |
| Gly | Thr | Val | His | Leu | Ile | Phe | Gln | Pro | Ala | Glu | Glu | Gly | Gly | Gly | Gly |      |
|     | 130 |     |     |     |     | 135 |     |     |     |     | 140 |     |     |     |     |      |
| gcg | cgc | gag | atg | gtc | gag | gac | ggc | ctg | ttc | acc | cag | ttc | ccc | atg | cag | 480  |
| Ala | Arg | Glu | Met | Val | Glu | Asp | Gly | Leu | Phe | Thr | Gln | Phe | Pro | Met | Gln |      |
| 145 |     |     |     |     | 150 |     |     |     |     | 155 |     |     |     |     | 160 |      |
| gcc | gtg | ttc | ggc | atg | cac | aac | tgg | ccg | ggc | atg | aag | gcc | ggc | acc | atg | 528  |
| Ala | Val | Phe | Gly | Met | His | Asn | Trp | Pro | Gly | Met | Lys | Ala | Gly | Thr | Met |      |
|     |     |     |     | 165 |     |     |     |     | 170 |     |     |     |     | 175 |     |      |
| ccg | tgg | gcc | ccg | ggc | ccg | gcc | atg | gcg | tcg | agc | aac | gag | ttc | cgc | atc | 576  |
| Pro | Trp | Ala | Pro | Gly | Pro | Ala | Met | Ala | Ser | Ser | Asn | Glu | Phe | Arg | Ile |      |
|     |     |     | 180 |     |     |     |     | 185 |     |     |     |     | 190 |     |     |      |
| gtc | gtg | cgc | ggc | aag | ggc | ggc | cac | gcg | gcc | atg | ccg | cac | atg | gtg | atc | 624  |
| Val | Val | Arg | Gly | Lys | Gly | Gly | His | Ala | Ala | Met | Pro | His | Met | Val | Ile |      |
|     |     | 195 |     |     |     |     | 200 |     |     |     |     | 205 |     |     |     |      |
| gac | ccg | ctg | ccc | gtg | gcg | gcc | cag | ctc | atc | ctg | ggc | ctg | cag | acc | atc | 672  |
| Asp | Pro | Leu | Pro | Val | Ala | Ala | Gln | Leu | Ile | Leu | Gly | Leu | Gln | Thr | Ile |      |
|     | 210 |     |     |     |     | 215 |     |     |     |     | 220 |     |     |     |     |      |
| gtc | agc | cgc | aac | gtc | aag | ccc | atc | gag | gcg | ggc | gtg | gtc | tcg | gtc | acc | 720  |
| Val | Ser | Arg | Asn | Val | Lys | Pro | Ile | Glu | Ala | Gly | Val | Val | Ser | Val | Thr |      |
| 225 |     |     |     |     | 230 |     |     |     |     | 235 |     |     |     |     | 240 |      |
| atg | gtc | cat | gcg | ggc | gag | gcc | acg | aac | gtg | gtg | ccc | gac | agc | gtg | gag | 768  |
| Met | Val | His | Ala | Gly | Glu | Ala | Thr | Asn | Val | Val | Pro | Asp | Ser | Val | Glu |      |
|     |     |     |     | 245 |     |     |     |     | 250 |     |     |     |     | 255 |     |      |
| ctg | cag | ggc | acg | gtg | cgc | acc | ttc | acg | ctg | gag | gtg | ctg | gac | ctg | atc | 816  |
| Leu | Gln | Gly | Thr | Val | Arg | Thr | Phe | Thr | Leu | Glu | Val | Leu | Asp | Leu | Ile |      |
|     |     |     | 260 |     |     |     |     | 265 |     |     |     |     | 270 |     |     |      |
| gag | cgg | cgc | atg | aag | gcc | ctg | gcc | gag | agc | atc | tgc | gcg | gcg | cat | gac | 864  |
| Glu | Arg | Arg | Met | Lys | Ala | Leu | Ala | Glu | Ser | Ile | Cys | Ala | Ala | His | Asp |      |
|     |     | 275 |     |     |     |     | 280 |     |     |     |     | 285 |     |     |     |      |
| acg | cgc | tgc | gag | ttc | gag | ttc | gtg | cgc | aac | tac | ccg | ccc | acc | atc | aac | 912  |
| Thr | Arg | Cys | Glu | Phe | Glu | Phe | Val | Arg | Asn | Tyr | Pro | Pro | Thr | Ile | Asn |      |
|     | 290 |     |     |     |     | 295 |     |     |     |     | 300 |     |     |     |     |      |
| tcc | gcc | ccg | gag | gcc | gag | ttc | gca | cgc | cgc | gtc | atg | gcc | gag | gtc | gtg | 960  |
| Ser | Ala | Pro | Glu | Ala | Glu | Phe | Ala | Arg | Arg | Val | Met | Ala | Glu | Val | Val |      |
| 305 |     |     |     |     | 310 |     |     |     |     | 315 |     |     |     |     | 320 |      |
| ggc | gag | gcc | aac | gtg | ctg | ccc | cag | gag | ccg | tcc | atg | ggc | gcc | gag | gac | 1008 |
| Gly | Glu | Ala | Asn | Val | Leu | Pro | Gln | Glu | Pro | Ser | Met | Gly | Ala | Glu | Asp |      |
|     |     |     |     | 325 |     |     |     |     | 330 |     |     |     |     | 335 |     |      |
| ttc | gcc | ttc | atg | ctg | ctg | gaa | aag | ccc | ggc | gcc | tac | tgc | ttc | atc | gcc | 1056 |
| Phe | Ala | Phe | Met | Leu | Leu | Glu | Lys | Pro | Gly | Ala | Tyr | Cys | Phe | Ile | Ala |      |
|     |     |     | 340 |     |     |     |     | 345 |     |     |     |     | 350 |     |     |      |
| aat | ggc | gac | ggc | gac | cac | cgc | gcc | atc | ggc | cac | ggc | ggc | ggt | ccc | tgc | 1104 |
| Asn | Gly | Asp | Gly | Asp | His | Arg | Ala | Ile | Gly | His | Gly | Gly | Gly | Pro | Cys |      |
|     |     | 355 |     |     |     |     | 360 |     |     |     |     | 365 |     |     |     |      |
| acg | ctg | cac | aac | ccc | agc | tac | gac | ttc | aac | gac | cag | ctg | att | ccg | cag | 1152 |
| Thr | Leu | His | Asn | Pro | Ser | Tyr | Asp | Phe | Asn | Asp | Gln | Leu | Ile | Pro | Gln |      |
|     | 370 |     |     |     |     | 375 |     |     |     |     | 380 |     |     |     |     |      |
| ggc | gcc | acg | ttc | tgg | gtg | aag | ctg | gcc | cag | cgc | tgg | ctg | agc | gag | ccc | 1200 |
| Gly | Ala | Thr | Phe | Trp | Val | Lys | Leu | Ala | Gln | Arg | Trp | Leu | Ser | Glu | Pro |      |
| 385 |     |     |     |     | 390 |     |     |     |     | 395 |     |     |     |     | 400 |      |
| acg | cgc | tgaggccttg | cggggtccgg | ccgacaccgg | catgtcacac | accgcaccta |     |     |     |     |     |     |     |     |     | 1256 |

Thr Arg gcatgcggtc cctgtga                                                                                             1273

<210> SEQ ID NO 4
<211> LENGTH: 402
<212> TYPE: PRT
<213> ORGANISM: Comamonas acidovorans

<400> SEQUENCE: 4

```
Met Ala Leu Leu Gln Glu Leu Leu Asp Ser Ala Pro Glu Ile Thr Ala
 1               5                  10                  15

Leu Arg Arg Asp Ile His Ala His Pro Glu Leu Cys Phe Glu Glu Leu
            20                  25                  30

Arg Thr Ala Asp Leu Val Ala Arg Gln Leu Glu Gly Trp Gly Ile Ala
        35                  40                  45

Val His Arg Gly Leu Gly Arg Thr Gly Val Val Gly Thr Ile His Gly
    50                  55                  60

Arg Asp Gly Gly Ala Ser Gly Arg Ala Ile Gly Leu Arg Ala Asp Met
65                  70                  75                  80

Asp Ala Leu Pro Met Gln Glu Phe Asn Thr Phe Glu His Ala Ser Arg
                85                  90                  95

His Ala Gly Lys Met His Ala Cys Gly His Asp Gly His Val Ala Met
            100                 105                 110

Leu Leu Ala Ala Ala Gln Tyr Leu Ala Val His Arg Asp Ser Phe Glu
        115                 120                 125

Gly Thr Val His Leu Ile Phe Gln Pro Ala Glu Glu Gly Gly Gly Gly
    130                 135                 140

Ala Arg Glu Met Val Glu Asp Gly Leu Phe Thr Gln Phe Pro Met Gln
145                 150                 155                 160

Ala Val Phe Gly Met His Asn Trp Pro Gly Met Lys Ala Gly Thr Met
                165                 170                 175

Pro Trp Ala Pro Gly Pro Ala Met Ala Ser Ser Asn Glu Phe Arg Ile
            180                 185                 190

Val Val Arg Gly Lys Gly Gly His Ala Ala Met Pro His Met Val Ile
        195                 200                 205

Asp Pro Leu Pro Val Ala Ala Gln Leu Ile Leu Gly Leu Gln Thr Ile
    210                 215                 220

Val Ser Arg Asn Val Lys Pro Ile Glu Ala Gly Val Val Ser Val Thr
225                 230                 235                 240

Met Val His Ala Gly Glu Ala Thr Asn Val Val Pro Asp Ser Val Glu
                245                 250                 255

Leu Gln Gly Thr Val Arg Thr Phe Thr Leu Glu Val Leu Asp Leu Ile
            260                 265                 270

Glu Arg Arg Met Lys Ala Leu Ala Glu Ser Ile Cys Ala Ala His Asp
        275                 280                 285

Thr Arg Cys Glu Phe Glu Phe Val Arg Asn Tyr Pro Pro Thr Ile Asn
    290                 295                 300

Ser Ala Pro Glu Ala Glu Phe Ala Arg Arg Val Met Ala Glu Val Val
305                 310                 315                 320

Gly Glu Ala Asn Val Leu Pro Gln Glu Pro Ser Met Gly Ala Glu Asp
                325                 330                 335

Phe Ala Phe Met Leu Leu Glu Lys Pro Gly Ala Tyr Cys Phe Ile Ala
            340                 345                 350
```

```
Asn Gly Asp Gly Asp His Arg Ala Ile Gly His Gly Gly Pro Cys
        355                 360             365

Thr Leu His Asn Pro Ser Tyr Asp Phe Asn Asp Gln Leu Ile Pro Gln
        370             375             380

Gly Ala Thr Phe Trp Val Lys Leu Ala Gln Arg Trp Leu Ser Glu Pro
385             390             395             400

Thr Arg
```

US 6,555,733 B2

GENES CODING FOR AMINO ACID DEACETYLASES WITH SPECIFICITY FOR N-ACETYL-L-PHOSPHINOTHRICIN, THEIR ISOLATION AND USE

CROSS-REFERENCE TO RELATED APPLICATIONS

This application is a divisional of U.S. Ser. No. 09/319,892, now U.S. Pat. No. 6,177,616, which corresponds to PCT/EP97/06755 filed Dec. 3, 1997, designating the U.S., which claims priority from German Patent Application 196 52 284.6 filed Dec. 16, 1996. Each of these documents are incorporated herein by reference.

BACKGROUND OF THE INVENTION

The concept of a chemically inducible, reversible male sterility in plants by anther-specific expression of an N-acetylphosphinothricin (N-acetyl-PPT)-specific deacetylase is described in European Patent Application EP 531 716. The deacetylase genes from *Streptomyces viridochromogenes* [N-acetyl-L-phosphinothricylalanylalanine (N-acetyl-PTT) deacetylase, dea] and argE from *Escherichia coli* (N-acetyl-L-ornithine deacetylase) used here encode proteins having specificity for N-acetyl-L-PPT. For both genes, it was possible in the case of tapetum-specific expression in plants to show the occurrence of male-sterile flowers after treatment of individual buds with N-acetyl-L-PPT. For successful use of this system, in particular in the treatment of whole plants with N-acetyl-PPT under practically relevant conditions, it is advantageous to be able to employ deacetylases having high substrate affinity. Therefore further deacetylases having high affinity for N-acetyl-PPT were sought.

OBJECTS OF THE INVENTION

The application described here is thus based on the object of making available DNA molecules which code for deacetylases. Using these deacetylases, it is possible to produce plants having plant parts which can be destroyed specifically. The production of male- or female-sterile plants is of particular interest. The object is achieved by the provision of the embodiments described in the patent claims.

SUMMARY OF THE INVENTION

The invention relates to DNA molecules which code for deacetylases or proteins with the biological activity of a deacetylase. The enzymatic properties of these proteins are described in the examples. The invention also relates to DNA molecules which encode a biologically active subfragment or a derivative. The molecules according to the invention also include fragments, derivatives or allelic variants. Fragments are understood as meaning parts which still have the biological activity of a deacetylase.

The invention additionally relates to transgenic plant cells which have been transformed using the DNA molecules according to the invention. The transgenic plant cells can be prepared according to known techniques and are regenerated to give whole plants.

The invention relates to DNA molecules encoding a protein having the biological activity of an N-acetyl-PPT deacetylase.

The invention relates in particular to DNA molecules encoding a protein having the biological activity of an N-acetyl-PPT deacetylase selected from the group consisting of a) DNA molecules which code for a protein having the amino acid sequence indicated under SEQ ID NO: 2 and fragments and/or derivatives thereof;

b) DNA molecules which code for a nucleotide sequence indicated under SEQ ID NO: 1 or sequences which deviate from this sequence within the bounds of code degeneracy;

c) DNA molecules which code for a protein having the amino acid sequence indicated under SEQ ID NO: 4 or fragments and/or derivatives thereof and d) DNA molecules which code for a nucleotide sequence indicated under SEQ ID NO: 3 or sequences which deviate from this sequence within the bounds of code degeneracy.

The invention additionally relates to the microorganisms Stenotrophomonas sp. (DSM 9734) and *Comamonas acidovorans* (DSM 11070) identified and deposited according to the method described in this application.

The invention relates in particular to plant cells or plants which contain the DNA molecules according to the invention.

Of particular interest are processes for the production of plants with specifically destroyable parts by means of specific expression of a deacetylase gene and processes for the production of male- or female-sterile plants by means of specific expression of a deacetylase gene.

The present application thus also relates to:

(1) the specific concentration of microorganisms having high N-acetyl-PPT deacetylase activity (2) the isolation of corresponding deacetylase genes (3) the purification and characterization of the proteins having high N-acetyl-PPT deacetylase activity encoded by these genes (4) the expression of the deacetylase genes in plants.

The present application additionally relates to:

the DNA molecules which code for enzymes having high N-acetyl-PPT deacetylase activity the proteins which are encoded by these genes the expression of these deacetylase genes in plants.

From soil samples, bacteria can be concentrated in mineral medium with chitin as the sole carbon source which are able to cleave N-acetyl-PPT with high effectiveness. In this manner, 2 bacterial strains were isolated as pure cultures: Stenotrophomonas sp. (DSM deposit No. DSM 9734) and *Comamonas acidovorans* (DSM deposit No. 11070).

For the conditions necessary in industrial production, however, it is substantially more advantageous to be able to employ a purified enzyme.

The present application comprises novel L-N-acetyl-PPT specific deacetylases, a novel and effective process for the purification and characterization of this enzyme from a concentration culture of soil microorganisms, and the use of this deacetylase.

The invention thus further relates to:

1. A deacetylase having a molecular weight of 20,000 to 100,000 Daltons a pH optimum of 6.5–10.0 a substrate specificity to L-N-acetyl-phosphinothricin.

2. A process for the preparation of a deacetylase, which comprises culturing a microorganism which does not form spores in a medium comprising crab chitin, and isolating the deacetylase from these microorganisms.

3. The use of the deacetylase characterized under 1. for the production of male-sterile plants and for the stereoselective preparation of L-phosphinothricin.

The invention relates in particular to an enzyme which has a temperature optimum which lies between 30° C. and 50° C.

DETAILED DESCRIPTION OF THE INVENTION

The process according to the invention for the preparation of the deacetyl-ases is preferably carried out using microorganisms selected from the group which consists of the microorganisms described in the application.

Crab chitin can be obtained as described by Shimahara, Kenzo and Takiguchi, Yasuyuki (Methods in Enzymology, Vol 161, pages 417–423, 1988) or is commercially available from Sigma.

To purify the deacetylase, the microorganism is cultured in a nutrient medium optimal for its growth. The microorganism is cultured aerobically, for example submerse with shaking or stirring in shaker flasks or fermenters, if appropriate with introduction of air or oxygen. The fermentation can be carried out in a temperature range from approximately 20 to 40° C., preferably at approximately 25 to 37° C., in particular at 30 to 37° C. Culture takes place in a pH range between 5 and 8.5, preferably between 5.5 and 8.0.

Under these conditions, the microorganisms in general show a noticeable accumulation of the enzyme after 1 to 3 days. The synthesis of the deacetylase begins with the log phase. The production of the enzyme can be monitored with the aid of activity tests by HPLC analysis or photometrically. The nutrient solution used for the production of the transaminase contains 0.2 to 5%, preferably 0.5 to 2%, of crab chitin and inorganic salts.

Inorganic salts which the nutrient medium can contain are, for example, chlorides, carbonates, sulfates or phosphates of the alkali metal or alkaline earth metals, iron, zinc and manganese, but also ammonium salts and nitrates.

According to the invention, effective amounts of the deacetylase can be employed in free or immobilized form for the deacetylation, preferably it is employed in plants which express dea genes.

For fixation, the known processes are suitable, such as the processes described in German Offenlegungsschriften 32 37 341 and 32 43 591.

The enzyme can be isolated and purified by classical methods by means of decomposition by ultrasound and French press, ammonium sulfate precipitation, ion exchangers, affinity chromatography and gel permeation.

The enzyme preparation can have a molecular weight of 20,000 to 100,000 Daltons, preferably 30,000 to 80,000, in particular 40,000 to 70,000 Daltons. The pH optimum of the enzyme product lies in the pH range 6.0 to 10.0, in particular 7.0 to 8.0. The temperature optimum of the enzyme lies between 30 and 50° C., in particular between 35 and 45° C.

The genes coding for the deacetylases were cloned in *E. coli*. In the case of the deac1 gene from Stenotrophomonas sp., a phagemid expression bank from genomic DNA in *E. coli* was screened for N-acetyl-PPT-specific deacetylase activity. The deac2 gene from *Comamonas acidovorans* was cloned with a genomic bank by complementation of an *E. coli*—argE mutant.

The amino acid sequences derived from the DNA sequences of the two genes are similar to one another and additionally have homology to hippurate hydrolases, as are known from protein databanks.

The high substrate affinity of the deac1 protein for N-acetyl-L-PPT ($K_m$=670 $\mu$M) makes itself noticeable in the transgenic plants by a high sensitivity of the tissue to this substance. Thus in constitutive expression of the deac gene plants can be obtained whose leaves still react sensitively to concentrations of up to 0.4 mg/ml of N-acetyl-D,L-PPT(= 0.2 mg/ml of L-enantiomer). In the case of tapetum-specific expression, the induction of male-sterile flowers was achieved by treatment of the buds with 2 mg/ml of N-acetyl-D,L-PPT(=1 mg/ml of L-enantiomer). The results described relate to greenhouse plants. On the basis of the low substance concentrations, if required, under open air conditions a higher dose of around 5–10-fold is possible without problems.

EXAMPLE

The following examples serve to illustrate the invention more extensively. Percentage data, if not stated otherwise, relate to the weight. The invention is defined further in the patent claims.

Example 1

Isolation and Identification of Soil Microorganisms Having an N-acetyl-PPT-specific Deacetylase Activity Each 1 g of soil (sandy loam, Schwanheimer dune) was extracted for 1 h at room temperature with 10 mM NaCl, 10 mM Na phosphate buffer, pH=7.0. To select various groups of microorganisms, the soil supernatants were transferred to the following liquid media:

(1) MS1 medium (for Eubacteria):
  5 mM glucose
  5 mM succinate
  10 mM glycerol
  1 g/l of $NH_4Cl$
  50 ml/l of solution A
  25 ml/l of solution B
  Solution A: 50 g/l of $K_2HPO_4$
  Solution B: 2.5 g/l of $MgSO_4$
  0.5 g/l of NaCl
  25 ml/l of trace elements
(2) Chitin medium (for Actino- and Streptomycetes, and chitinovorous bacteria):
  10 g/l of crab chitin
  1 g/l of $(NH_4)_2SO_4$
  0.5 g/l of $MgSO_4$
  50 ml/l of solution A
  1 ml/l of trace elements
(3) Antibiotic medium (for higher fungi):
  20 g/l of malt extract
  10 g/l of glucose
  2 g/l of yeast extract
  0.5 g/l of $(NH_4)_2SO_4$
  50 $\mu$g/ml of tetracycline All media contained 5 mM N-acetyl-PPT and were incubated for 3–5 days at 28° C. after transferring.

The concentration cultures were then tested for deacetylation of N-acetyl-PPT. To do this, the cells were centrifuged off at 10,000 rpm and the supernatants were investigated for formation of PPT in an amino acid analyzer (Biotronic LC 5001). Only the chitin medium cultures proved to be deactylase-positive. After plating out on chitin-agar, a total of 40 individual colonies were isolated from these cultures, recultured in chitin liquid medium and tested again for deacetlyase activity. Six positive isolates were found here, from which it was possible to obtain the active pure cultures by repeated streaking out on agar plates and further culturing of individual colonies. The strain with the highest deacetylase activity was identified as Stenotrophomonas sp. (DSM deposit No. DSM 9734).

Example 2

Cloning and Sequencing of the N-acetyl-PPT Deactylase Gene from Stenotrophomonas sp The standard molecular biology methods used for the studies are described in Maniatis et al. 1982, Molecular Cloning: a laboratory manual, Cold Spring Harbor Laboratory, Cold Spring Harbor, N.Y.

Genomic DNA from Stenotrophomonas sp. was prepared according to the method of Meade et al., 1982, J. Bacteriol. 149:114–122. After partial digestion with Sau3A, the 5–10 kb size fraction was isolated and ligated in the lambda-ZAP express vector, which was cleaved with BamHI, from Stratagene (ZAP Express Vector Kit, Catalog No. 239201, Instruction Manual). Using the packaged ligation batch, a primary lambda-phage bank was prepared and then amplified. A phagemid expression bank in *Escherichia coli* was prepared from this with the aid of the pBK-CMV phagemid system from Stratagene (Catalog No. 212209, Instruction Manual). This gene bank was tested for the presence of the deactylase gene by activity screening with [$^{14}$C]-N-acetyl-L-PPT as a substrate. For this purpose, 2000 individual clones were transferred to microtiter plates and cultured overnight in LB medium at 37° C. with 0.2 mM isopropyl thiogalactoside (IPTG) as an inducer and 50 µg/ml of kanamycin as a resistance marker. The cells were centrifuged off and incubated overnight at 28° C. in 10 µl each of 1 mM [$^{14}$C]-N-acetyl-L-PPT. The batches were then analyzed in pools of eight for conversion of N-acetyl-PPT into PPT by thin-layer chromatography and autoradiography (see EP 531 716, Example 8) and the individual clones retested in the case of a positive result. Using this method, it was possible to select from 1920 transformants a positive clone having a 6 kb insert. This DNA fragment was characterized in greater detail by restriction mapping. By subcloning restriction fragments of the inserts in pUC18/19 and transformation of the recombinant plasmids in *E. coli*, it was possible with the aid of the activity test described above to localize the deac structural gene on a 2.5 kb (2487 base pairs) SalI/SmaI fragment (FIG. 1). The activity was dependent on the orientation of the fragment relative to the lac promoter of the vector.

The 2.5 kb fragment was sequenced on both strands using the Sanger method (Sanger et al. 1977, Proc. Natl. Acad. Sci USA 74:5463–5468). The entire fragment has a length of 2487 nucleotides (see SEQ ID NO: 1). The open reading frame of 1494 nucleotides length begins with nucleotide No. 367 and ends with No. 1860.

Expression studies with PCR subfragments from this region in *E. coli* showed that the active deacetylase protein is encoded by a region 1365 nucleotides long beginning with the ATG start codon in position 496 and ending with the TGA stop codon in position 1860. The amino acid sequence derived from the DNA sequence is a polypeptide of 454 amino acids (Seq ID NO:2) having a calculated molecular weight of 48.1 kDa.

A homology search in the EMBL, DNA and protein databanks showed similarities to the N-acetyl-PPT deacetylase from *Comamonas acidovorans* described in this application for the first time (37.4% identical amino acids), the hippurate hydrolase from *Campylobacter jejuni* (33.9%) and N-acyl-L-amidohydrolase from *Bacillus stearothermophilus* (33.7%). Below, the gene isolated from Stenotrophomonas is described as deac1. The corresponding protein is described as Deac1. On account of the homology, it can be assumed that the hippurate hydrolases and amidohydrolases mentioned can also advantageously be used in combination with tissue-specific promoters and a subsequent treatment for the preparation of plants having selectively destroyable tissues, in particular male and/or female-sterile plants.

Example 3

Characterization of the Deac1 Protein

To overexpress and purify the deactylase from Stenotrophamonas sp. (deac1), the glutathione S-transferase (GST) gene fusion vector system from Pharmacia (Catalog No. 27-4581-01, Catalog No. 27-4570-01) was used. The method is described in Smith and Johnson, 1988, Gene 67:31. The fusion proteins are purified by affinity chromatography on glutathione-Sepharose 4B.

The functional deac gene was recloned into the GST fusion vector pGEX-4T-2 under control of the lac promoter as a 1.4 kb BamHI/SalI PCR fragment. The expression of recombinant fusion protein was induced by addition of 0.1 mM IPTG. By SDS/polyacrylamide electrophoresis of crude extracts of the *E. coli* transformants, it was possible to detect the fusion protein as a 74 kDa band.

To purify the protein, the cells of a 2 l culture of an induced, expression-positive *E. coli* transformant were disrupted with ultrasound and the extract was then solubilized by addition of 1% Triton X-100. The supernatant was bound to glutathione-Sepharose 4B. After repeated washing with PBS buffer (140 mM NaCl, 3 mM KCL, 10 mM $Na_2HPO_4$, 2 mM $KH_2PO_4$, pH=7.3), the fusion protein bound to the Sepharose matrix was cleaved with thrombin. The eluate contained as the only protein band a cleavage product of 48 kDa (after denaturing SDS/polyacrylamide electrophoresis), which was identified in the enzyme assay (see below) as N-acetyl-PPT deactylase. Using the method described, it was possible to purify 200 µg of deacetylase protein to homogeneity from 2 l of bacterial culture.

The activity of the deacetylase protein was measured using the two following assays:

(1) Radioactive test: 2.5 µg each of purified enzyme was incubated with 0.1 mM [$^{14}$C]-N-acetyl-L-PPT for 15 min. at 37° C. in 10 µl batches in PBS buffer. The samples were then diluted 1:6 in 5 mM $KH_2PO_4$, 10% methanol, pH=1.92 and analyzed in the HPLC using a radioactivity detector (separating column: Spherisorb SAX, eluent: 5 mM $KH_2PO_4$, 10% methanol, pH=1.92, flow rate: 0.5 ml/min). Under these conditions, [$^{14}$C]-L-PPT elutes at 4.5 min. and[$^{14}$C]-N-acetyl-L-PPT elutes at 6.5 min. The specific deacetylase activities were determined in [nmol of [$^{14}$C]-L-PPT/min/mg of protein]. To determine the pH optimum, the batches were incubated between pH=6 and 9 in a buffer system of, in each case, 40 mM bis-tris, tris and caps. For the $K_m$ value measurement, 3-fold determinations were carried out at pH=8.0 in the presence of 1 mM $CoCl_2$ using concentrations of [$^{14}$C]-N-acetyl-L-PPT of between 0.01 mM and 1 mM.

(2) Nonradioactive test: To investigate the substrate specificity, 5 µg each of purified enzyme were incubated for 60 min. at 28° C. in 20 µl batches in PBS buffer with, in each case, 25 mM of a certain N-acetyl- or N-acylamino acid. The samples were then measured in an amino acid analyzer (Biotronic LC 5001) for formation of the free amino acids. The specific activities were determined in [nmol of amino acid/min/mg of protein]. For the N-acetyl-PPT deacetylase, a pH optimum of pH=8 (see Tab. 1) and a temperature optimum of 37° C. (see Tab. 2) were determined. The kinetic measurements showed a $K_m$ value of 670 μM. By addition of 1 mM $CoCl_2$, the enzyme activity could be increased by about 20%.

TABLE 1 pH optimum of the N-acetyl-PPT deacetylase

| pH | Spec. activity [mol/min/mg of protein] |
|---|---|
| 6 | 2.4 |
| 7 | 7.2 |
| 8 | 12.0 |
| 9 | 8.5 |

TABLE 2

Temperature optimum of the N-acetyl-PPT deacetylase

| Temperature [° C.] | Spec. activity [nmol/min/mg of protein]: |
|---|---|
| 28 | 9.6 |
| 37 | 16.8 |
| 50 | 14.9 |
| 60 | 4.3 |

The results of the measurements of substrate specificity are shown in Tab. 3.

The enzyme has a relatively wide substrate spectrum. The highest conversions were achieved with hippuric acid (N-benzoylglycine) and N-acetyl-L-glutamate. The affinity for N-acetyl-L-PPT lies approximately 50% below that for the two abovementioned substrates. The deacetylase has an exclusive specificity for N-acetyl-L-amino acids. Using the corresponding D-enantiomers, no reactions were observed.

TABLE 3

Substrate specificity of the N-acetyl-PPT deacetylase

| Substrate[1] | Rel. activity[2] [%] |
|---|---|
| Hippuric acid (N-benoylglycine) | 100 |
| N-Ac-phosphinothricin | 43 |
| N-Ac-ornithine | 37 |
| N-Ac-methionine | 0 |
| N-Ac-tryptophan | 0.4 |
| N-Ac-phenylalanine | 24 |
| N-Ac-tyrosine | 11 |
| N-Ac-glutamic acid | 100 |
| N-Ac-glutamine | 30 |
| N-Ac-glycine | 59 |
| N-Ac-histidine | 43 |
| N-Ac-leucine | 33 |
| N-Ac-valine | 2 |

TABLE 3-continued

Substrate specificity of the N-acetyl-PPT deacetylase

| Substrate[1] | Rel. activity[2] [%] |
|---|---|
| N-Ac-serine | 4 |
| N-Ac-proline | 0 |

[1]In all compounds these are the L-enantiomers.
[2]The specific activity measured with hippuric acid was set equal to 100% and the other values were related to it.

Example 4

Constitutive Expression of the Deac1 Gene in Tobacco

The deac1 structural gene was recloned as a 1.4 kb BamHI/SalI PCT fragment into the binary vector pPCV801 (Koncz and Schell, 1986, Mol. Gen. Genet. 204: 383–396) under control of the 35S promoter. The resulting plasmid pPCVKDEAC1 (FIG. 2) with the expression vector 35S promoter-deac1-structural gene-35S terminator was transformed in Agrobacterium tumefaciens (strain ATHV) using standard methods. Pieces of tobacco leaf (Nicotiana tabacum) were transformed with the recombinant Agrobacteria according to the method of Horsch et al., 1985, Science 227: 1229–1231 and selected on kanamycin medium, 18 independent tobacco transformants were regenerated and tested for expression of the deacetylase in the leaves. In the case of activity of the protein in the transgenic plants, a sensitivity of the leaves to N-acetyl-PPT was to be expected, because the substance in the plant is then converted into the herbicidal active compound phosphinothricin on account of the enzymatic activity of the deacetylase.

In a drop experiment, the leaves of the transgenic plants and of a number of nontransgenic control plants were treated with 5 μl each of the following concentrations of N-acetyl-D,L-PPT: 4 mg/ml(=15 mM), 1 mg/ml(=3.75 mM), 0.4 mg/ml(=1.5 mM), 0.1 mg/ml(=0.38 mM). The treatment sites were examined for lightening or necrosis formation after 1–2 weeks. Simultaneously, the N-acetyl-PPT-specific deacetylase activity of the transformants, and also of the control plants, was measured in crude extracts. To do this, 100 mg each of leaf material were homogenized in 200 μl of PBS buffer, the cell debris was centrifuged off and the protein-containing supernatants were dialyzed overnight at 4° C. against the same buffer. 10 μl each of these samples were incubated with 0.1 mM [$^{14}$C]-N-acetyl-L-PPT overnight at 37° C. The batches were then analyzed in the HPLC, as described above, for formation of [$^{14}$C]-L-PPT.

The test results of the drop experiments and the activity tests are shown in Tab. 4 for selected plants. It is seen that about 60% of the transformants express the functional deacetylase protein and show the corresponding phenotype.

TABLE 4

Sensitivity of pPCVKDEAC1 plants to N-acetyl-PPT and deacetylase activity in crude extracts

| | Drop experiment with: N-Ac-D,L-PPT | | | | Deac. activity in the crude extract |
|---|---|---|---|---|---|
| Plants | Observations (leaf:) | 4 mg/ml | 1 mg/ml | 0.4 mg/ml | 0.1 mg/ml | [% L-PPT][1] |
| Control | | – | – | – | – | 0 |
| pPCVK9 | | +++ | + | – | – | 14.2 |

TABLE 4-continued

Sensitivity of pPCVKDEAC1 plants to N-acetyl-PPT and deacetylase activity in crude extracts

| Plants | Drop experiment with: N-Ac-D,L-PPT Observations (leaf:) | Deac. activity in the crude extract | | | | [% L-PPT][1] |
|---|---|---|---|---|---|---|
| | | 4 mg/ml | 1 mg/ml | 0.4 mg/ml | 0.1 mg/ml | |
| pPCVK14 | curled | + | + | − | − | 12.1 |
| pPCVK15 | curled | ++ | + | + | − | 36.0 |
| pPCVK16 | curled | + | + | − | − | 4.7 |
| pPCVK17 | curled | + | + | − | − | 4.3 |

[1]based on the radioactivity employed ([$^{14}$C]-N-acetyl-L-PPT)

+++: severe necrosis
++: marked damage
+: slight lightening
−: no symptoms

Example 5

Tapetum-specific Expression of the Deac1 Gene in Tobacco

Using standard methods, the tapetum-specific promoter of the tap1 gene from snapdragon (Antirrhinum majus) was fused in the vector pUC18 as a 2.2 kb EcoRI/BamHI fragment with the deac1 structural gene (1.4 kb BamHI/SalI-PCR fragment) and the 35S terminator. The expression cassette tap1 promoter-deac structural gene-35S terminator thus resulting was cloned into the binary vector pPCV801 as a 3.8 kb EcoRI fragment instead of the 35S promoter/terminator region (plasmid pPCVTDEAC1, FIG. 3). The transformation of tobacco was carried out as described in Example 4.

In the case of tapetum-specific expression of the deacetylase, it should be possible by treatment of the flower buds with N-acetyl-PPT to induce male-sterile flowers. The conversion of the PPT derivative into the herbicidal active compound phosphinothricin leads to selective damage to the tapetum tissue, by means of which the development of functional pollen is prevented.

In each case only one side of the inflorescences (the total area of the developing flower buds) was treated with N-acetyl-PPT, the other side of the influorescences remained untreated in order to ensure that the phenomena to be observed are not to be attributed to deformities of the respective plants. The treatment was carried out at a time at which the individual buds were not larger than 5 mm (active phase for tapetum promoter). The tobacco transformants and also a number of NT Sam NN control plants were treated 3× with 0.2% N-acetyl-D,L-PPT(=7.5 mM)/0.1% Genapol (wetting agent) within one week. After the blooming of the buds (about 9–11 days after conclusion of the treatment), the plants were investigated for the occurrence of male-sterile flowers.

Simultaneously, the N-acetyl-PPT-specific deacetylase activity in immature anthers of the transformants, and also of the control plants, was measured. To do this, the immature anthers were dissected from flower buds about 5 mm in size and incubated overnight at room temperature in 50 μM [$^{14}$C]-N-acetyl-L-PPT solution in each case. The anthers were subsequently washed 1× in 500 μl of PBS buffer and then homogenized in 50 μl of PBS buffer. After centrifuging off the cell debris, the supernatants were concentrated in a Speed-Vac and the pellets were taken up in 30 μl each of HPLC buffer (5 mM KH$_2$PO$_4$, 10% methanol, pH=1.92). The batches were analyzed for formation of [$^{14}$C]-L-PPT in the HPLC, as described above.

The results of the flower treatment and of the activity test are shown for selected plants in Tab. 5. In almost all transformants, it was possible to determine an anther-specific deacetylase activity. In 3 transformants, male-sterile flowers, i.e. no pollen was formed, or severely pollen-reduced flowers were observed on the side of the flower cluster treated with N-acetyl-PPT. The effects on new, maturing buds lasted for a period of about 3 weeks. The untreated flowers of the transformants, and also the treated flowers of the control plants, were fertile in all cases. With the male-sterile flowers, no seed formation was determinable. A specific cross pollination of the male-sterile flowers was possible, however, by means of which it was proven that the female flower parts have kept their full functionality (Nacken et al, 1991, Mol.Gen. Genet. 229: 129–136).

TABLE 5

Induced male sterility in pPCVTDEAC1 plants by flower treatment with N-acetyl-PPT and deacetylase activity in anthers

| Plant | Number of sterile or pollen-reduced flowers | | Deac. activity in anthers |
|---|---|---|---|
| | treated | untreated | [% L-PPT][1] |
| Control | 0 | 0 | 0 |
| pPCVT14 | 18 | 0 | 70.0 |
| pPCVT15 | 0 | 0 | 13.8 |
| pPCT16 | 10 | 0 | 20.4 |

[1]based on the radioactivity employed ([$^{14}$C]-N-acetyl-L-PPT)

Example 6

Isolation and Identification of a Deacetylase Having Specificity for N-acetylphosphinothricin from *Comamonas Acidovorans*

A soil sample from Bangkok was suspended in mineral salt medium (0.5 g of $K_2HPO_4$, 0.2 g of $MgSO_4$, 2 g of $(NH_4)_2SO_4$, 0.01 g of $FeSO_4$ in 980 ml of $H_2O$), which contained chitin (2 g/l) as the only carbon source and subsequently incubated at 30° C. for 48 hours. Transfer to fresh mineral salt medium then took place and after incubation for a further 48 hours dilution series were plated out on LB medium (Miller, Experiments in molecular genetics, Cold Spring Harbour Laboratory Press).

Among the growing colonies, also found were those of a bacterial strain which distinguishes itself in pure culture by a very good utilization of N-acetyl glutamate as the only carbon source (streaking-out on mineral salt medium with N-acetyl glutamate (2 g/l, add as a sterile-filtered solution to autoclaved mineral salt medium with 14 g/l of agar) leads in the course of incubation at 30° C. for 12 hours to the formation of clearly visible colonies). The deacetylation of N-acetyl-PPT was detected as described above. The strain provided with the laboratory description B6 was identified by the DSM as *Comamonas acidovorans* (DSM 11070).

Example 7

Cloning of the Deactylase Gene from *Comamonas Acidovorans*

Total DNA from *Comamonas acidovorans* was isolated, digested with EcoRI and ligated with likewise EcoRI-digested DNA of the vector pACYC184 (Cang and Cohen, 1978, J. Bacteriol. 134,1141–1156). The ligation batch was used for the electroporation of the *E. coli* argE mutant XSID2 (Mountain et al., 1984, Mol. Gen. Genet. 197, 82–89). By selection for complementation of the arginine auxotrophy, it was possible to isolate an EcoRI fragment 8.9 kb in size from the genome of *C. acidovorans*, which is adequate for the complementation. By subcloning, the complementing region could be restricted to a fragment 1.4 kb in size. This is present in the derivative designated by pGK83 of the sequencing vector pSVB30 (Arnold and P ühler, 1988, Gene 70,172–178).

Example 8

Sequencing of the Deacetylase Gene from *Comamonas Acidovorans*

The complementing fragment 1.4 kb (1387 base pairs) in size was completely sequenced as a double strand by known methods.

Example 9

Coding Region Analysis and Homology Comparison of the Sequenced Region

A coding region analysis showed an open reading frame from position 1 to 1206 (SEQ ID NO: 3), which codes for a protein 402 amino acids in size (SEQ ID NO: 4).

The homology comparison with known genes from databanks shows a clear homology to an N-acyl-L-amidohydrolase from *Bacillus stearothermophilus* (ama, Sakanyan et al., 1993, Appl. Environ. Microbiol. 59, 3878–3888) and a hippurate hydrolase from *Campylobacter jejuni* (hitherto unpublished). In the protein comparison, the hippurate hydrolase has 43% of identical amino acids (Tab. 6). Moreover, at the DNA and protein level, the gene has a very conspicuous homology to the deacetylase gene isolated from Stenotrophomonas spec. Following the designation of the gene from Stenotrophomonas sp., the gene identified from *C. acidovorans* was designated by deac2.

TABLE 6

Homology comparison with known sequences

| Gene | Organism | Function | ident. AA | cons. AA |
|---|---|---|---|---|
| n.n | *Campylobacter jejuni* | Hippurate hydrolase (383 AS) | 43.1% | 60.0% |
| deac2 | *Bacillus stearothermophilus* | N-acyl-L-amido-hydrolase (370 A3) | 37.0% | 49.5% |

Example 10

Overexpression of the Deac2 Gene from *Comamonas Acidovorans* Plant Constructs

To analyze the substrate specificity of the deac2 gene product from *Comamonas acidovorans*, this was overexpressed. To do this, the gene was cloned into a vector with a high copy number under control of the lacZ promoter. The expression efficiency, however, was restricted by the simultaneous translation, taking place in another reading frame, of the lacZ-alpha. This was therefore interrupted by introducing a stop codon, such that the vector pGK81 makes possible an overexpression of the deac2 gene which is not adversely effected by the lacZ gene. It was also possible to detect this phenotypically, since this construct has a markedly higher complementation of an *E. coli* argE mutant.

For the transformation of plants, the deac2 structural gene was recloned using the binary vector pROK1 (Baulcombe et al. 1986, Nature, 321: 446–449) after the constitutive 35S promoter or the tapetum-specific promoter TA-29. The expression plasmids pGK83 and pMF9 obtained are shown in the figures.

Example 11

Investigation of the Substrate Specificity of the Deac2 Gene Product from *Comamonas Acidovorans*

To investigate the substrate specificity of the deac2 gene product from *Comamonas acidovorans*, cells of *E. coli* strain XLI blue permeabilized by toluene/ethanol treatment were used with and without the vector pGK81. The induction of the deac2 gene repressed by the $Lac^i$ repressor present in this strain could be achieved by IPTG treatment. The permeabilized cells were incubated for 3 hours at 30° C. with various N-acetylated amino acids (final concentration 25 mM) and the supernatants were investigated with the aid of an amino acid analyzer. It turned out here that more than 20% of the N-acetylornithine made available was converted. For N-acetyl-phosphinothricin too, an increasing deacetylation to phosphinothricin, analogous to the concentration of N-acetylphosphinothricin employed, could be found (Table 7).

TABLE 7

Conversion of N-acetylated amino acids by the deac2 gene product

| N-acetyl-ornithine | N-acetyl-phenylalanine | N-acetylphosphinothricin | | |
|---|---|---|---|---|
| (25 mM) | (25 mM) | (12.5 mM) | (25 mM) | (50 mM) |
| 5860 nM | <5 nM | 8.0 nM | 20.0 nM | 44.7 nM |

The concentrations of the N-acetylated amino acids employed and the amino acids formed by deacetylation are indicated.

Figure 1:
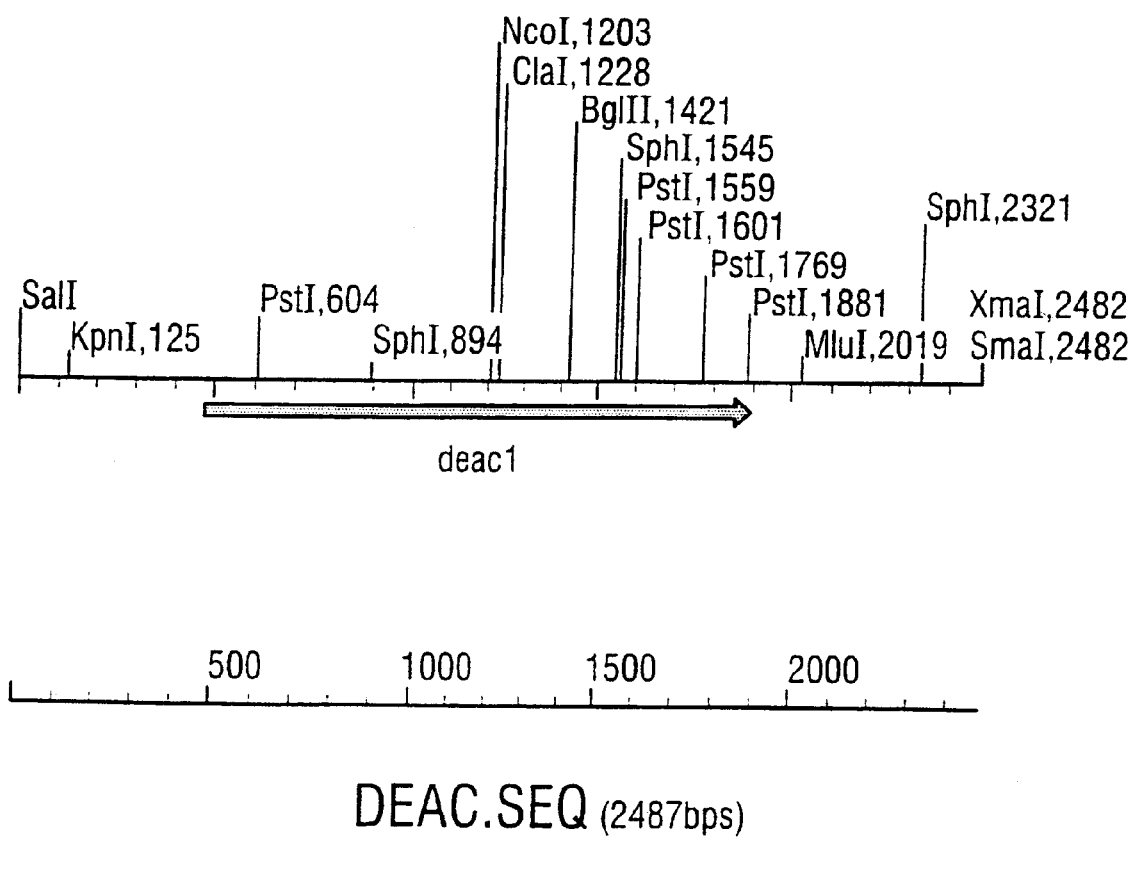
FIG. 1 Restriction map of the 2.5 kb SalI/BamHI fragment which mediates the N-acetyl-PPT-specific deacetylase activity. Position and orientation of the deac1 structural gene are marked by an arrow (BP=base pairs).
Figure 2:
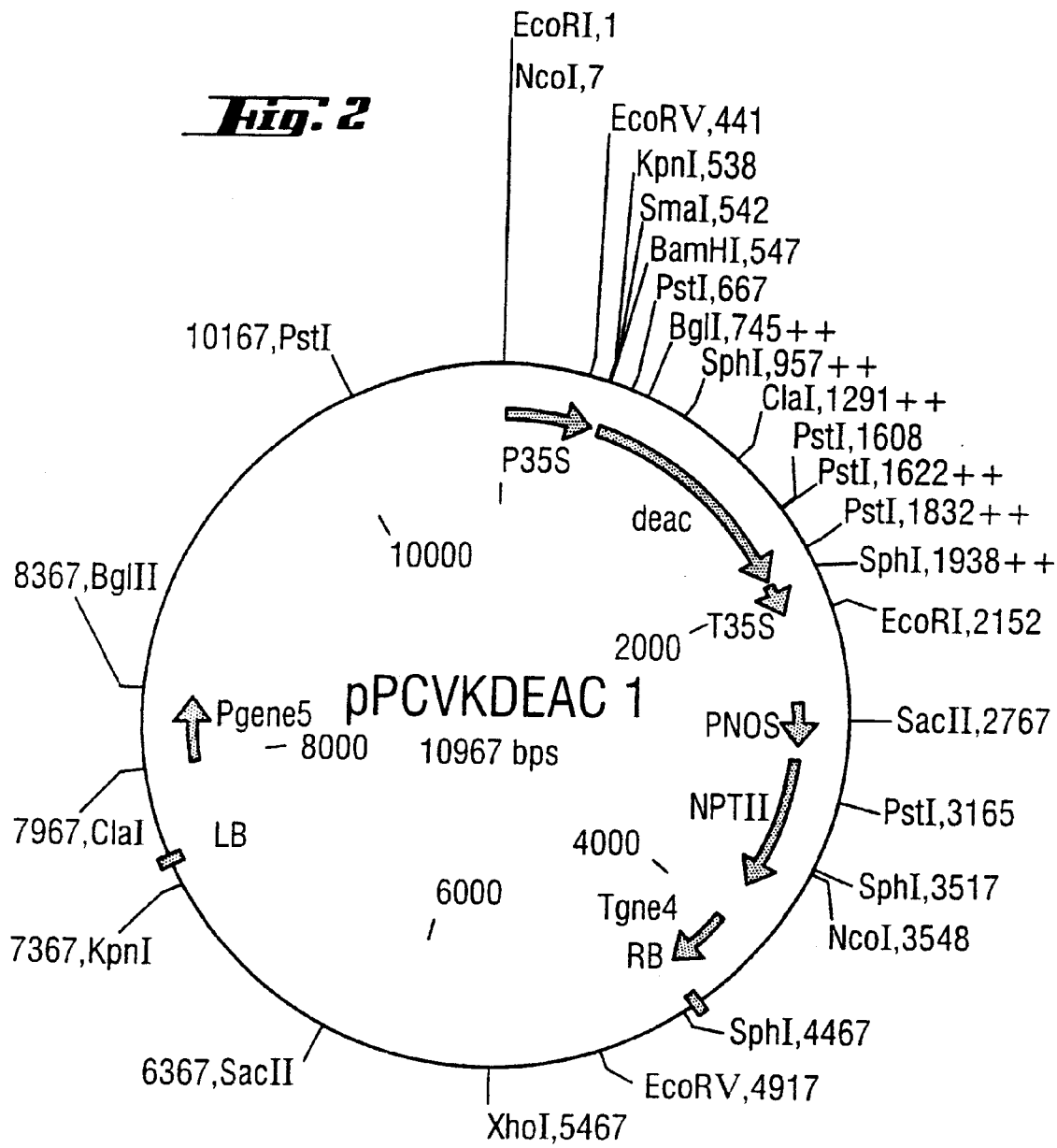
FIG. 2 Map of the plasmid pPVCKDEAC1 for the constitutive expression of the deac gene in plants FIG. 3 Map of the plasmid pPCVTDEAC1 for the tapetum-specific expression of the deac gene in plants FIG. 4 Map of the plasmid pGK83
Figure 3:
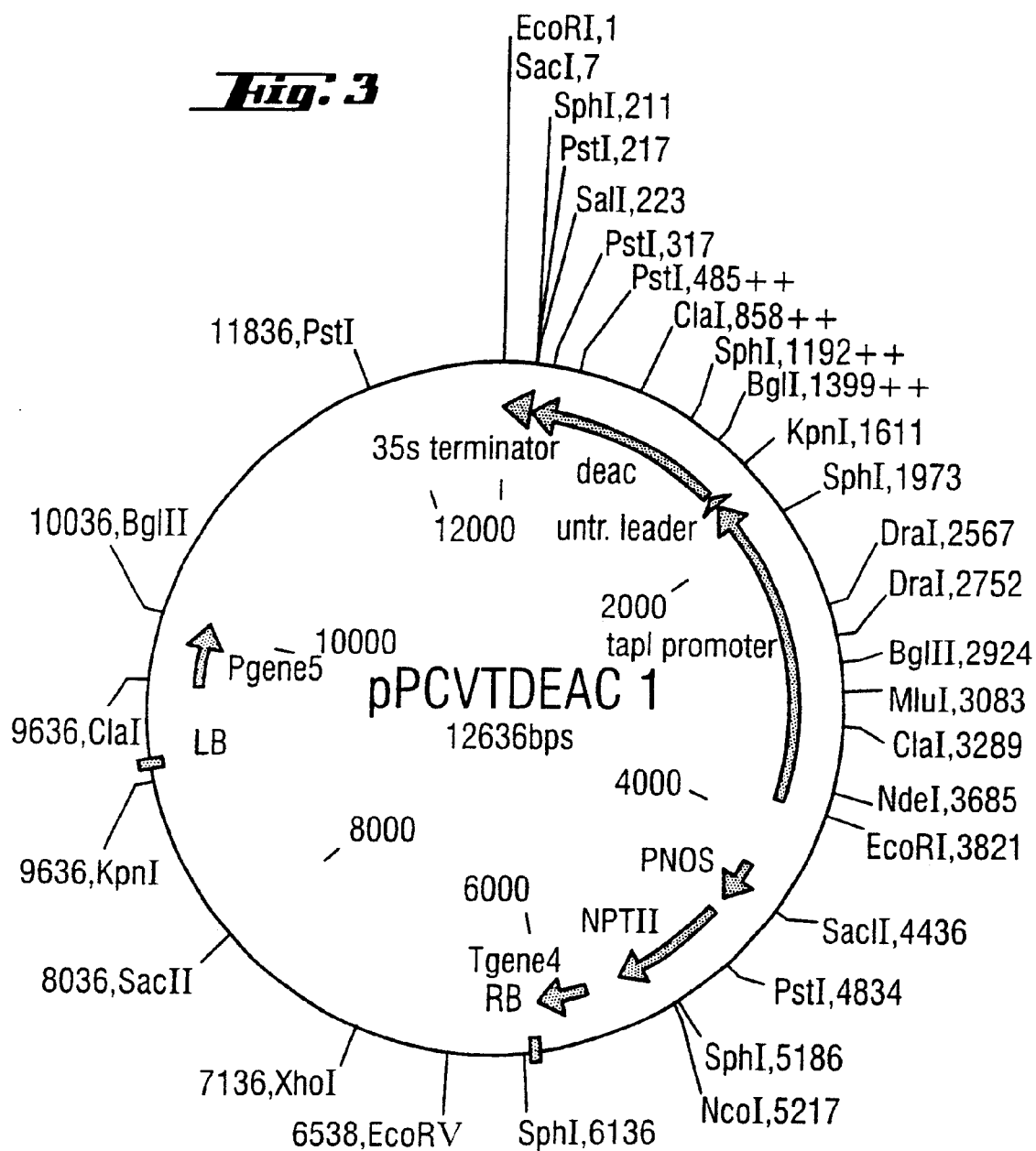
Figure 4:
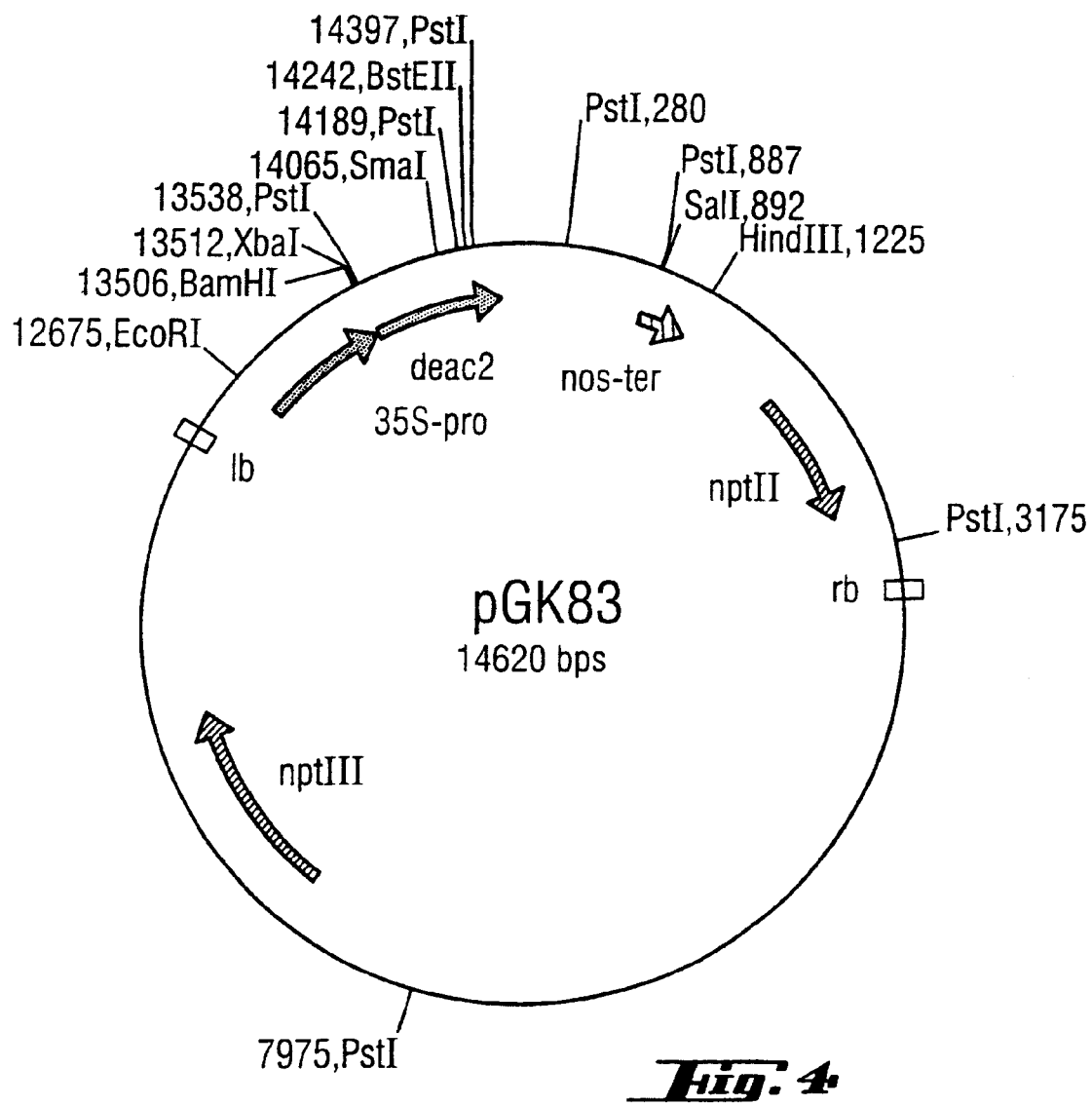
Figure 5:
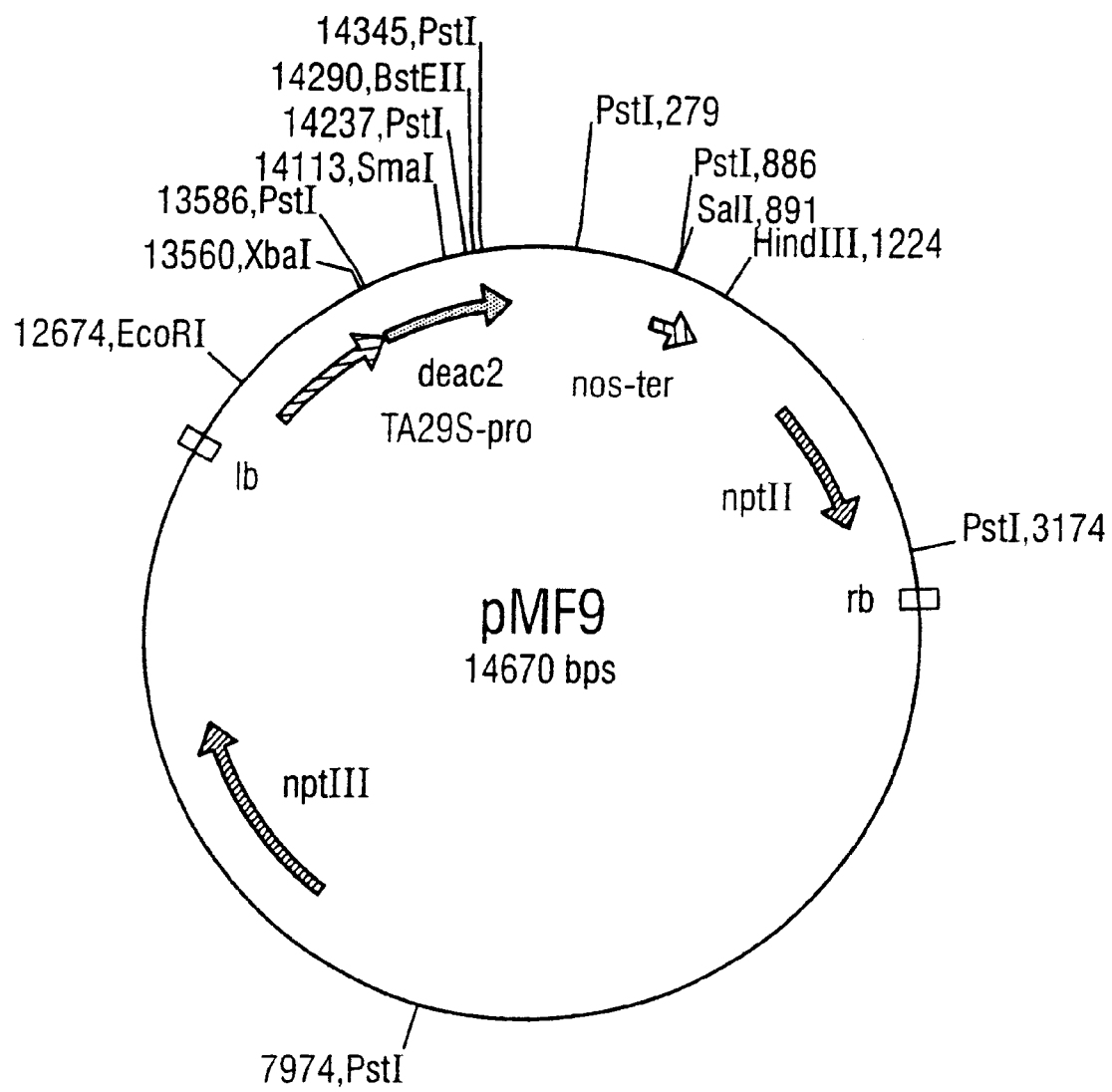
FIG. 5 Map of the plasmid pMF9

[illegible]
INTERNATIONAL FORM

Hoechst Schering AgrEvo GmbH
Forschung Biochemie H 872 N

65926 Frankfurt/Main

RECEIPT IN THE CASE OF AN ORIGINAL
DEPOSIT issued pursuant to Rule 7.1 by
the INTERNATIONAL DEPOSITARY AUTHORITY
identified at the bottom of this page

| I. IDENTIFICATION OF THE MICROORGANISM | |
|---|---|
| Identification reference given by the DEPOSITOR:<br><br>3010 | ACCESSION NUMBER issued by the INTERNATIONAL DEPOSITARY AUTHORITY:<br><br>DSM 9734 |

| II. SCIENTIFIC DESCRIPTION AND/OR PROPOSED TAXONOMIC DESIGNATION |
|---|
| The microorganism identified under I was accompanied by:<br>    ( )    a scientific description<br>    ( )    a proposed taxonomic designation<br>(Mark with a cross where applicable) |

| III. RECEIPT AND ACCEPTANCE |
|---|
| This International Depositary Authority accepts the microorganism identified under I above, which was received by it on 14-02-1995 (date of the initial deposit)[1]. |

| IV. RECEIPT OF A REQUEST FOR CONVERSION |
|---|
| This International Depositary Authority received the microorganism identified under I above on     (date of the initial deposit) and received a request for conversion of the initial deposit conforming to the Budapest Treaty on (date of receipt of the request for conversion). |

| V. INTERNATIONAL DEPOSITARY AUTHORITY | |
|---|---|
| Name:    DSM-DEUTSCHE SAMMLUNG VON MIKROORGANISMEN UND ZELLKULTUREN GmbH<br><br>Address:    Mascheroder Weg 1b<br>                D-38124 Braunschweig | Signature(s) of person(s) having the power to represent the International Depositary Authority or of an authorized official(s)<br><br>(illegible signature)<br><br>Date:    21-02-1995 |

[1] Where Rule 6.4.d) applies, such date is the date on which the status of international depositary authority was acquired.

[illegible]
INTERNATIONAL FORM

Prof. Dr. A. Pühler

Lefrstuhl für Genetik
Universität Bielefeld
P.O. Box 100131
D-33501 Bielefeld

RECEIPT IN THE CASE OF AN ORIGINAL
DEPOSIT issued pursuant to Rule 7.1 by
the INTERNATIONAL DEPOSITARY AUTHORITY
identified at the bottom of this page

| I. IDENTIFICATION OF THE MICROORGANISM | |
|---|---|
| Identification reference given by the DEPOSITOR: | ACCESSION NUMBER issued by the INTERNATIONAL DEPOSITARY AUTHORITY: |
| B6 | DSM 11070 |

II. SCIENTIFIC DESCRIPTION AND/OR PROPOSED TAXONOMIC DESIGNATION

The microorganism identified under I was accompanied by:
    ( )   a scientific description
    (X)   a proposed taxonomic designation
(Mark with a cross where applicable)

III. RECEIPT AND ACCEPTANCE

This International Depositary Authority accepts the microorganism identified under I above, which was received by it on 12-07-1996 (date of the initial deposit)[1].

IV. RECEIPT OF A REQUEST FOR CONVERSION

This International Depositary Authority received the microorganism identified under I above on    (date of the initial deposit) and received a request for conversion of the initial deposit conforming to the Budapest Treaty on (date of receipt of the request for conversion).

V. INTERNATIONAL DEPOSITARY AUTHORITY

| | |
|---|---|
| Name:    DSM-DEUTSCHE SAMMLUNG VON MIKROORGANISMEN UND ZELLKULTUREN GmbH<br>Address:  Mascheroder Weg 1b<br>          D-38124 Braunschweig | Signature(s) of person(s) having the power to represent the International Depositary Authority or of an authorized official(s)<br><br>(illegible signature)<br><br>Date:    16-07-1996 |

[1] Where Rule 6.4.d) applies, such date is the date on which the status of international depositary authority was acquired.

Form DSMZ-BP/4 (single page) 0196

---

What is claimed is:

1. An isolated DNA molecule encoding a protein having the biological activity of an N-Acetyl-Phosphinothricin deacetylase and having the amino acid sequence of SEQ ID NO: 2.

2. An isolated DNA molecule encoding a protein having the biological activity of an N-Acetyl-Phosphinothricin deacetylase, which comprises the nucleotide sequence indicated under SEQ ID NO: 1 or a sequence that deviates from this sequence within the bounds of code degeneracy.

3. A method of producing plants with inducibly destroyable parts, the method comprising the steps of:
   a) transforming plant cells with a deacetylase gene comprising the DNA sequence as claimed in claim 1 or 2, encoding a protein having the biological activity of a deacetylase, under the control of a promoter directing expression in specific plant parts; and
   b) regenerating said plants from said plant cells, wherein said plants have parts which can be inducibly destroyed by treatment with N-acetyl-PPT.

4. The method of claim 3, wherein said plants can be made male sterile or female sterile by the specific expression of said deacetylase gene.

5. The method of claim 3, wherein said promoter is a tapetum-specific promoter.

6. The method of claim 3, wherein said promoter is the TA29 promoter or the tap1 promoter.

7. A plant cell which comprises the isolated DNA molecule as claimed in claim 1 or 2.

8. A plant which comprises the isolated DNA molecule as claim 1 or 2.

9. A plant which can be made male-sterile or female sterile by treatment with N-acetyl-PPT due to the specific expression therein of a deacetylase gene comprising the isolated DNA molecule of claim 1 or 2.

10. The plant of claim 9, which can be made male-sterile, wherein said deacetylase gene is under control of a tapetum-specific promoter.

11. The plant of claim 10, wherein said promoter is the TA29 promoter.

12. The plant of claim 10, wherein said promoter is the promoter of the tap1 gene from snapdragon.

13. The plant of claim 9, which is made male sterile by application of N-acetyl PPT.

14. The plant of claim 9, which can be made female sterile.

15. The plant of claim 10, which is made male sterile by application of N-acetyl PPT.

16. The plant of claim 11, which is made male sterile by application of N-acetyl PPT.

17. The plant of claim 12, which is made male sterile by application of N-acetyl PPT.

* * * * *